(12) United States Patent
Crockford

(10) Patent No.: US 8,093,214 B2
(45) Date of Patent: Jan. 10, 2012

(54) METHOD OF TREATING OR PREVENTING TISSUE DETERIORATION, INJURY OR DAMAGE DUE TO CONGESTIVE HEART FAILURE

(75) Inventor: David Crockford, Newburyport, MA (US)

(73) Assignee: Regenerx Biopharmaceuticals, Inc., Bethesda, MD (US)

( * ) Notice: Subject to any disclaimer, the term of this patent is extended or adjusted under 35 U.S.C. 154(b) by 684 days.

(21) Appl. No.: 11/996,021

(22) PCT Filed: Jul. 26, 2006

(86) PCT No.: PCT/US2006/028996
§ 371 (c)(1),
(2), (4) Date: Jun. 27, 2008

(87) PCT Pub. No.: WO2007/014253
PCT Pub. Date: Feb. 1, 2007

(65) Prior Publication Data
US 2009/0117187 A1    May 7, 2009

Related U.S. Application Data

(60) Provisional application No. 60/702,269, filed on Jul. 26, 2005.

(51) Int. Cl.
*A61K 38/00* (2006.01)
*A61P 9/00* (2006.01)
(52) U.S. Cl. .................................................. 514/16.4
(58) Field of Classification Search .................. None
See application file for complete search history.

(56) References Cited

U.S. PATENT DOCUMENTS

| 7,268,118 | B2 * | 9/2007 | Kleinman et al. | 514/17 |
| 7,816,321 | B2 * | 10/2010 | Nie et al. | 530/399 |
| 2003/0060405 | A1 | 3/2003 | Kleinman et al. | |
| 2004/0220111 | A1 | 11/2004 | Kleinman et al. | |

FOREIGN PATENT DOCUMENTS

| JP | 04-234325 | * | 8/1992 |
| JP | 2005-502672 A | | 1/2005 |
| WO | WO 0006190 | * | 2/2000 |
| WO | WO 0236143 | * | 5/2002 |
| WO | 03/020215 A2 | | 3/2003 |
| WO | 2004/091550 A2 | | 10/2004 |

OTHER PUBLICATIONS

Abstract in English for JP 04-234325, Aug. 1992. 2 pages.*
Calvin et al., Hemodynamic monitoring: a technology assessment, Can. Med. Assoc. J. 1991, 145(2):114-121.
Crockford, David, "Development of Thymosin Beta-4 for Treatment of Patients with Ischemic Heart Disease," Annals of the New York Academy of Sciences, Sep. 2007, vol. 1112, pp. 385-395.
Smart, Nicola et al., "Thymosin Beta-4 is Essential for Coronary Vessel Development and Promotes Neovascularization via Adult Epicardium," Annals of the New York Academy of Sciences, Sep. 2007, vol. 1112, pp. 171-188.
Srivastava Deepak et al., "Thymosin B-4 is Cardioprotective after Myocardial Infarction," Annals of the New York Academy of Sciences, Sep. 2007, vol. 1112, pp. 161-170.
I. Bock-Marquette et al.: "Thymosin β4 activates integrin-linked kinase and promotes cardiac cell migration, survival and cardiac repair," Nature, vol. 432, Nov. 25, 2004, pp. 466-472.

* cited by examiner

*Primary Examiner* — Marcela M Cordero Garcia
(74) *Attorney, Agent, or Firm* — Rothwell, Figg, Ernst & Manbeck, P.C.

(57) ABSTRACT

A method of treatment for treating, preventing, inhibiting or reducing tissue deterioration, injury or damage due to congestive heart failure disease, or for restoring tissue adversely affected by said disease, in a subject, includes administering to a subject an effective amount of a composition including a peptide agent including amino acid sequence LKKTET [SEQ ID NO: 1] or LKKTNT [SEQ ID NO: 2], a conservative variant thereof, or a peptide agent that stimulates production of an LKKTET [SEQ ID NO: 1] or LKKTNT [SEQ ID NO: 2] peptide, or a conservative variant thereof, in the tissue.

15 Claims, No Drawings

METHOD OF TREATING OR PREVENTING TISSUE DETERIORATION, INJURY OR DAMAGE DUE TO CONGESTIVE HEART FAILURE

CROSS-REFERENCE TO RELATED APPLICATION

This application is a 35 U.S.C. §371 National Phase Entry Application of PCT/US2006/028996, filed 26 Jul. 2006, and claims the benefit of U.S. Provisional application Ser. No. 60/702,269, filed 26 July 2005.

BACKGROUND OF THE INVENTION

1. Field of the Invention

The present invention relates to the field of treating or preventing tissue deterioration, injury or damage due to congestive heart failure.

2. Description of the Background Art

Congestive heart failure (CHF) disease is manifested in an imbalance in heart pump function in which the heart fails to maintain the circulation of blood adequately. The most severe manifestation of CHF, pulmonary edema, develops when this imbalance causes an increase in lung fluid secondary to leakage from pulmonary capillaries into the interstitium and alveoli of the lung.

CHF can be categorized as forward or backward ventricular failure. Backward failures is secondary to elevated systemic venous pressure, while left ventricular failure is secondary to reduced forward flow into the aorta and systemic circulation. Furthermore, heart failure can be subdivided into systolic and diastolic dysfunction. Systolic dysfunction is characterized by a dilated left ventricle with impaired contractility, while diastolic dysfunction occurs in a normal or intact left ventricle with impaired ability to relax and receive as well as eject blood.

The New York Heart Association's functional classification of CHF is one of the most useful. Class I describes a patient who is not limited with normal physical activity by symptoms. Class II occurs when ordinary physical activity results in fatigue, dyspnea, or other symptoms. Class III is characterized by a marked limitation in normal physical activity. Class IV is defined by symptoms at rest or with any physical activity.

CHF is summarized best as an imbalance in Starling forces or an imbalance in the degree of end-diastolic fiber stretch proportional to the systolic mechanical work expended in an ensuing contraction. This imbalance may be characterized as a malfunction between the mechanisms that keep the interstitium and alveoli dry and the opposing forces that are responsible for fluid transfer to the interstitium.

Maintenance of plasma oncotic pressure (generally about 25 mm Hg) higher than pulmonary capillary pressure (about 7-12 mm Hg), maintenance of connective tissue and cellular barriers relatively impermeable to plasma proteins, and maintenance of an extensive lymphatic system are the mechanisms that keep the interstitium and alveoli dry.

Opposing forces responsible for fluid transfer to the interstitium include pulmonary capillary pressure and plasma oncotic pressure. Under normal circumstances, when fluid is transferred into the lung interstitium with increased lymphatic flow, no increase in interstitial volume occurs. When the capacity of lymphatic drainage is exceeded, however, liquid accumulates in the interstitial spaces surrounding the bronchioles and lung vasculature, thus creating CHF. When increased fluid and pressure cause tracking into the interstitial space around the alveoli and disruption of alveolar membrane junctions, fluid floods the alveoli and leads to pulmonary edema.

In the U.S., more than 3 million people have CHF, and more than 400,000 new patients present yearly. Prevalence of CHF is 1-2% of the general population.

Approximately 30-40% of patients with CHF are hospitalized every year. CHF is the leading diagnosis-related group among hospitalized patients older than 65 years. The 5-year mortality rate after diagnosis was reported in 1971 as 60% in men and 45% in women. In 1991, data showed the 5-year mortality rate of CHF essentially remaining unchanged, with a median survival of 3.2 years for males and 5.4 years for females. This may be secondary to an aging U.S. population with declining mortality due to other diseases.

The most common cause of CHF death is progressive heart failure, but sudden death may account for up to 45% of all deaths. After auditing data on 4606 patients hospitalized with CHF between 1992-1993, the total in-hospital mortality rate was 19%, with 30% of deaths occurring from noncardiac causes.

There remains a need in the art for methods of treatment for treating, preventing, inhibiting or reducing tissue deterioration, injury or damage due to congestive heart failure.

SUMMARY OF THE INVENTION

In accordance with one aspect, a method of treatment for treating, preventing, inhibiting or reducing tissue deterioration, injury or damage due to congestive heart failure disease, or for restoring tissue adversely affected by said disease, in a subject, comprises administering to a subject in need of such treatment an effective amount of a composition comprising a peptide agent comprising amino acid sequence LKKTET [SEQ ID NO: 1] or LKKTNT [SEQ ID NO: 2], a conservative variant thereof, or a stimulating agent that stimulates production of an LKKTET [SEQ ID NO: 1] or LKKTNT [SEQ ID NO: 2] peptide, or a conservative variant thereof, in said tissue, so as to inhibit said tissue deterioration, injury or damage due to congestive heart failure disease, or restore tissue adversely affected by said disease.

DETAILED DESCRIPTION OF THE INVENTION

Congestive heart failure, also called heart failure, is a disorder in which the heart loses its ability to pump blood efficiently and can no longer keep up with the normal demands placed on it. As a consequence of conditions that damage or weaken heart muscle and cause the ventricles to stretch (dilate), the failing pump does not move blood efficiently throughout the circulatory system. Blood starts to back up, increasing the pressure in the blood vessels and forcing fluid from the vessels into body tissues. This condition may affect the right side, the left side or both sides of the heart. Typically, heart failure begins to fail (left-sided heart failure/left ventricular heart failure), the back pressure of blood forces fluid to collect in the lungs (pulmonary edema). This extra fluid in the lungs makes it more difficult for the airways to expand during inhalation. Breathing becomes more difficult and shortness of breath (dyspnea) occurs. When the right side of the heart starts to fail (right-sided heart failure), there's a back pressure of blood trying to enter the heart causing fluid to collect in the feet, ankles and lower legs. As the heart failure worsens, the upper legs swell and eventually the abdomen collects fluid (ascites). Weight gain accompanies the fluid retention. Puffy swelling (peripheral edema) is a sigh of right heart failure, especially if the edema is pitting edema. This buildup of fluid in the lungs, legs, feet, ankles, liver and abdomen is the congestive part of heart failure.

The development of CHF is progressive and is generally a chronic, long-term condition, although it may develop suddenly following a heart attach or an inflammatory disease of the heart muscle, such as dilated or restrictive cardiomyopathy, or the like.

Dilated (congestive) cardiomyopathy is the most common form and occurs due to enlarging and stretching (cardiac dilation) of the heart cavity, weakening the heart so it pumps abnormally. Abnormal heart rhythms (arrhythmias) and disturbances of the heart's electrical conduction may also occur. The cause of the condition is unknown in many cases, but it can be caused by a virus, autoimmune diseases such as rheumatoid arthritis, and excess alcohol consumption. Additionally, blood flows more slowly and turbulently through an enlarged and arrhythmic heart, leading to the formation of blood clots.

Restrictive Cardiomyopathy is the least common type of cardiomyopathy and develops when damaged heart muscle is replaced by fibrous scar and fatty tissue. The right side of the heart, including the atrium may first thicken and later dilate, i.e., become thinner. It may lead to disordered electrical activity and in some cases with the heart's pumping action. For the most part the ventricles become so stiff that it's hard for them to fill with blood between contractions.

CHF becomes more common with advancing age. Risk factors include obesity, diabetes, tobacco usage, alcohol abuse, cocaine usage.

Etiology

The most common cause of congestive heart failure is coronary artery disease (atherosclerosis), which weakens the heart by leaving some areas of myocardium chronically deprived of oxygen rich blood and nutrients. Consequently, these areas of the heart pump less vigorously. In many cases, blood flow to myocardium is just enough to keep the muscle alive but not functioning well. In other cases, a heart attack occurs when blood flow is completely blocked to an area of the heart muscle. Regions of myocardial death weaken the overall ability of the heart to pump.

Another important cause of CHF is hypertension, resulting in left ventricular heart failure. If blood pressure is high, the heart has to work harder than it should to circulate blood throughout the body. Over time, the heart muscle may become thicker to compensate for the extra work it must perform, but to no or little avail. In some cases the heart will enlarge. Eventually, heart muscle may become either too stiff or too weak to pump blood effectively.

Other structural or functional causes of heart failure include valvular heart disease (incompetent or stenotic), congenital heart disease, dystrophinopathies, idiopathic dilated cardiomyopathy (heart muscle disease/damage/weakness of unknown origin), prolonged serious arrhythmias, and lung disease (e.g., pulmonary arterial hypertension).

CHF Classification

Systolic heart failure: The pumping action of the left ventricle is reduced or weakened causing it to lose its ability to contract vigorously. A common clinical measurement of left ventricular function is the ejection fraction. Patients with systolic heart failure have a decreased ejection fraction of less than 50% (usually around 40% or less). A normal ejection fraction is greater than 50%.

Diastolic heart failure: The left ventricle appears to contract normally but it has lost its ability to relax or fill fully (i.e., it is stiff, or less compliant, when it is relaxing and filling with blood). This impedes blood filing into the heart and produces backup into the lungs. Diastolic heart failure is more common in individuals over the age of 75. In diastolic heart failure ejection fraction is normal.

Without being found to any specific theory, actin-sequestering peptides such as thymosin β4 (Tβ4 or TB4) and other agents including actin-sequestering peptides or peptide fragments containing amino acid sequence LKKTET [SEQ ID NO: 1] or LKKTNT [SEQ ID NO: 2], or conservative variants thereof, promote reversal or prevention of tissue deterioration, injury or damage due to congestive heart failure disease.

Thymosin beta 4 was initially identified as a protein that is up-regulated during endothelial cell migration and differentiation in vitro. Thymosin beta 4 was originally isolated from the thymus and is a 43 amino acid, 4.9 kDa ubiquitous polypeptide identified in a variety of tissues. Several roles have been ascribed to this protein including a role in a endothelial cell differentiation and migration, T cell differentiation, actin sequestration, vascularization and wound healing.

In accordance with one embodiment, the invention is a method of treatment for treating, preventing, inhibiting or reducing tissue deterioration, injury or damage due to congestive heart failure disease, or for restoring tissue adversely affected by said disease, in a subject, comprising administering to a subject in need of such treatment an effective amount of a composition comprising a peptide agent, which may be a polypeptide comprising amino acid sequence LKKTET [SEQ ID NO: 1] or LKKTNT [SEQ ID NO: 2], or a conservative variant thereof having congestive heart failure disease-inhibiting activity, preferably Thymosin β4, and/or Tβ4 isoforms, analogues or derivatives, including KLKKTET [SEQ ID NO: 3], LKKTETQ [SEQ ID NO: 4], oxidized Tβ4, N-terminal variants of Tβ4, C-terminal variants of Tβ4 and the like.

In preferred embodiments, the tissue deterioration, injury or damage comprises at least one of an increase in heart size or mass, increase in size or mass of heart tissue, thickening of heart muscle, or pulmonary edema.

Compositions which may be used in accordance with the present invention include peptide agents such as Thymosin β4 (Tβ4), and/or Tβ4 isoforms, analogues or derivatives, including oxidized Tβ4, N-terminal variants of Tβ4, C-terminal variants of Tβ4 and antagonists of Tβ4, polypeptides or peptide fragments comprising or consisting essentially of the amino acid sequence LKKTET [SEQ ID NO: 1] or LKKTNT [SEQ ID NO: 2], or conservative variants thereof, having congestive heart failure disease-inhibiting activity. International Application Serial No. PCT/US99/17282, incorporated herein by reference, discloses isoforms of Tβ4 which may be useful in accordance with the present invention as well as amino acid sequence LKKTET [SEQ ID NO: 1] and conservative variants thereof, which may be utilized with the present invention. International Application Serial No. PCT/GB99/00833 (WO 99/49883), incorporated herein by reference, discloses oxidized Thymosin β4 which may be utilized in accordance with the present invention. Although the present invention is described primarily hereinafter with respect to Tβ4 and Tβ4 isoforms, it is to be understood that the following description is intended to be equally applicable to amino acid sequence LKKTET [SEQ ID NO: 1] or LKKTNT [SEQ ID NO: 2], peptides and fragments comprising or consisting essentially of LKKTET [SEQ ID NO: 1]or LKKTNT [SEQ ID NO: 2], conservative variants thereof having congestive heart failure disease-inhibiting activity, and/or Tβ4 isoforms, analogues or derivatives, including oxidized Tβ4, N-terminal variants of Tβ4, C-terminal variants of Tβ4 and the like.

In one embodiment, the invention provides a method of treatment for treating, preventing, inhibiting or reducing tissue deterioration, injury or damage due to congestive heart failure disease, or for restoring tissue adversely affected by said disease, in a subject, by contacting heart tissue with an effective amount of a composition which contains a peptide agent as described herein. The contacting may be directly or systemically. Examples of direct administration include, for example, contacting the tissue, by direct application or inhalation, with a solution, lotion, salve, gel, cream, paste, spray, suspension, dispersion, hydrogel, ointment, foam or oil comprising a peptide agent as described herein. Systemic administration includes, for example, intravenous, intraperitoneal, intramuscular injections of a composition containing a peptide agent as described herein, in a pharmaceutically acceptable carrier such as water for injection.

Peptide agents for use in the invention, as described herein, may be administered in any effective amount. For example, a peptide agent as described herein may be administered in dosages within the range of about 0.0001-1,000,000 micrograms, more preferably in amounts within the range of about 0.1-5,000 micrograms, most preferably within the range of about 1-30 micrograms.

A composition in accordance with the present invention can be administered daily, every other day, every other week, every other month, etc., with a single application or multiple applications per day of administration, such as applications 2, 3, 4 or more times per day of administration.

Many Tβ4 isoforms have been identified and have about 70%, or about 75%, or about 80% or more homology to the known amino acid sequence of Tβ4. Such isoforms include, for example, Tβ4$^{ala}$, Tβ9, Tβ10, Tβ11, Tβ12, Tβ13, Tβ14 and Tβ15. Similar to Tβ4, the Tβ10 and Tβ15 isoforms have been shown to sequester actin. Tβ4, Tβ10 and Tβ15, as well as these other isoforms share an amino acid sequence, LKKTET [SEQ ID NO: 1] or LKKTNT [SEQ ID NO: 2], that appears to be involved in mediating actin sequestration or binding. Although not wishing to be bound by any particular theory, the activity of peptide agents as described herein may be due, at least in part, to the anti-inflammatory and/or actin modulating activity of such agents. Tβ4 modulates actin polymerization (e.g. β-thymosins appear to depolymerize F-actin by sequestering free G-actin). T Tβ4's ability to modulate actin polymerization may be due to its ability to bind to or sequester actin via the LKKTET [SEQ ID NO: 1] or LKKTNT [SEQ ID NO: 2] sequence. Thus, as with Tβ4, other proteins which are anti-inflammatory and/or bind or sequester actin, or modulate actin polymerization, including Tβ4 isoforms having the amino acid sequence LKKTET [SEQ ID NO: 1] or LKKTNT [SEQ ID NO: 2], are likely to be effective, alone or in a combination with Tβ4, as set forth herein.

Peptide agents as described herein, such as Tβ4 and Tβ4 isoforms, decrease inflammatory chemokine, cytokine and capase activity.

Thus, it is specifically contemplated that known Tβ4 isoforms, such as Tβ4$^{ala}$, Tβ9, Tβ10, Tβ11, Tβ12, Tβ13, Tβ14 and Tβ15, as well as Tβ4 isoforms not yet identified, will be useful in the methods of the invention. As such Tβ4 isoforms are useful in the methods of the invention, including the methods practiced in a subject. The invention therefore further provides pharmaceutical compositions comprising Tβ4, as well as Tβ4 isoforms Tβ4$^{ala}$, Tβ9, Tβ10, Tβ11, Tβ12, Tβ13, Tβ14 and Tβ15, and a pharmaceutically acceptable carrier.

In addition, other agents or proteins having anti inflammatory activity and/or actin sequestering or binding capability, or that can mobilize actin or modulate actin polymerization, as demonstrated in an appropriate sequestering, binding, mobilization or polymerization assay, or identified by the presence of an amino acid sequence that mediates actin binding, such as LKKTET [SEQ ID NO: 1] or LKKTNT [SEQ ID NO: 2], for example, can similarly be employed in the methods of the invention. Such proteins may include gelsolin, vitamin D binding protein (DBP), profilin, cofilin, depactin, Dnasel, vilin, fragmin, severin, capping protein, .beta.-actinin and acumentin, for example. As such methods include those practiced in a subject, the invention further provides pharmaceutical compositions comprising gelsolin, vitamin D binding protein (DBP), profilin, cofilin, depactin, Dnasel, vilin, fragmin, severin, capping protein, p-actinin and acumentin as set forth herein. Thus, the invention includes the use of an polypeptide comprising the amino acid sequence LKKTET [SEQ ID NO: 1] or LKKTNT [SEQ ID NO: 2] and conservative variants thereof.

As used herein, the term "conservative variant" or grammatical variations thereof denotes the replacement of an amino acid residue by another, biologically similar residue. Examples of conservative variations include the replacement of a hydrophobic residue such as isoleucine, valine, leucine or methionine for another, the replacement of a polar residue for another, such as the substitution of arginine for lysine, glutamic for aspartic acids, or glutamine for asparagine, and the like.

Tβ4 has been localized to a number of tissue and cell types and thus, agents which stimulate the production of an LKKTET [SEQ ID NO: 1] or LKKTNT [SEQ ID NO: 1] peptide such as Tβ4 or another peptide agent as described herein, can be added to or comprise a composition to effect production a peptide agent from a tissue and/or a cell. Such stimulating agents may include members of the family of growth factors, such as insulin-like growth factor (IGF-1), platelet derived growth factor (PDGF), epidermal growth factor (EGF), transforming growth factor beta (TGF-β), basic fibroblast growth factor (bFGF), thymosin α1 (Tα1) and vascular endothelial growth factor (VEGF). More preferably, the stimulating agent is transforming growth factor beta (TGF-β) or other members of the TGF-β superfamily.

In accordance with one embodiment, subjects are treated with a stimulating agent that stimulates production in the subject of a peptide agent as defined herein.

Additionally, other agents that assist in reduction of tissue deterioration, injury or damage due to congestive heart failure disease, or restoring tissue adversely affected by said disease may be added to a composition along with a peptide agent as described herein. For example, and not by way of limitation, a peptide agent as described herein alone or in combination can be added in combination with any one or more of the following agents: antibiotics, VEGF, KGF, FGF, PDGF, TGFβ, IGF-1, IGF-2, IL-1, prothymosin α and/or thymosin α1 in an effective amount.

The invention also includes a pharmaceutical composition comprising a therapeutically effective amount of a peptide agent as described herein in a pharmaceutically acceptable carrier. Such carriers include those listed herein.

The actual dosage or reagent, formulation or composition that provides treatment may depend on many factors, including the size and health of a subject. However, persons of ordinary skill in the art can use teachings describing the methods and techniques for determining clinical dosages as disclosed in PCT/US99/17282, supra, and the references cited therein, to determine the appropriate dosage to use.

Suitable formulations may include a peptide agent as described herein at a concentration within the range of about 0.001-50% by weight, more preferably within the range of about 0.01-0.1% by weight, most preferably about 0.05% by weight.

The therapeutic approaches described herein involve various routes of administration or delivery of a peptide agent as described herein, including any conventional administration techniques (for example, but not limited to, direct administration, local injection, inhalation, or systemic administration), to a subject. The methods and compositions using or containing a peptide agent as described herein may be formulated into pharmaceutical compositions by admixture with pharmaceutically acceptable non-toxic excipients or carriers.

The invention includes use of antibodies which interact with, enhance or inhibit a peptide agent as described herein. Antibodies which consist essentially of pooled monoclonal antibodies with different epitopic specificities, as well as distinct monoclonal antibody preparations are provided. Monoclonal antibodies are made from antigen containing fragments of the protein by methods well known to those skilled in the art as disclosed in PCT/US99/17282, supra. The term antibody as used in this invention is meant to include monoclonal and polyclonal antibodies.

In yet another embodiment, the invention provides a method of treating a subject by administering an effective amount of stimulating agent which modulates gene expression. The term "modulate" refers to inhibition or suppression of expression when a peptide agent as described herein is over expressed, and induction of expression when a peptide agent as described herein is underexpressed. The term "effective amount" means that amount of stimulating agent which is effective in modulating gene expression of a peptide agent as described herein, resulting in reducing the symptoms of tissue deterioration, injury or damage due to congestive heart failure disease, or restoring tissue adversely affected by said disease. A stimulating agent which modulates gene expression of a peptide agent as described herein may be a polynucleotide, for example. The polynucleotide may be an antisense, a triplex agent, or a ribozyme. For example, an antisense directed to the structural gene region or to the promoter region of a peptide agent as described herein may be utilized. The stimulating agent which modulates gene expression of a peptide agent as described herein may also be a small interfering RNAs (siRNAs).

In another embodiment, the invention provides a method for utilizing compounds that modulate activity of a peptide agent as described herein. Compounds that affect activity of a peptide agent as described herein (e.g., antagonists and agonists) include peptides, peptidomimetics, polypeptides, chemical compounds, minerals such as zincs, and biological agents.

A method for screening for a stimulating agent as defined herein, comprises contacting heart tissue exhibiting congestive heart failure disease, with a candidate compound; and measuring activity in said tissue of an LKKTET [SEQ ID NO: 1] or LKKTNT [SEQ ID NO: 2] peptide, wherein an increase of activity of said peptide in said tissue, compared to a level of activity of said peptide in a corresponding tissue lacking said candidate compound, indicates that said compound is capable of inducing said stimulating agent.

EXAMPLE 1

Study of Thymosin β4 in Mouse Myocardial Infarction (MI) Heart Failure Model

Objective:

The objective of the present study was to evaluate the effect of thymosin β4 in mouse MI-induced heart failure model.
Models The procedures used in this study are exactly same as that reported in Nature (432:466-472, 2004). Briefly, C57 black mice, 14 weeks old, were used in this study. Mice were given thymosin β4 (Bachem, Lot # FTHYB40501B) (150 µg/mouse) immediately after myocardial infarction and then every three days for 4 weeks by i.p. injection. The parameters of this study included cardiac morphology and function by echocardiography (echo), invasive cardiac function measurement using Millar catheter, survival rate, and histochemical analysis.

A heart attack (myocardial infarction) may rapidly lead to cardiac arrest (no heartbeat) or permanent damage of the left ventricle. If the damage is bad enough, regions of the heart may not function properly, which may lead to heart failure. In Nature 2004 (cited above) it was shown that TB4 was able to improve fractional shortening and ejection fraction when administered immediately following a heart attack in the mouse model. In this case the drug was administered accurately and functional improvements were demonstrated. Although functional improvements are critical for patient survival, no data were presented to suggest that TB4 would be able to attenuate or improve outcome following the significant damage that resulted from the heart attack induced in the animal model. Consequently, it was not obvious that TB4 would be able to treat a resulting heart failure that would follow in the surviving animals.

The present study suggests that TB4 is effective in treating mammals with heart failure/congestive heart failure (CHF). In this case TB4 was also administered acutely. However, in practice the drug may be administered acutely and/or chronically following an Acute Myocardial Infarction (AMI) or chronically in patients with progressive heart failure to stop the progression and worsening of the symptoms of CHF.

Hemodynamic Improvements:
Ventricular Pressure Reductions:

Treatment with TB4 showed a trend in improvement (i.e., a reduction) of left ventricular systolic pressure (LVSP) following heart muscle damage/injury. Hypertension and/or increased ventricular systolic pressures are/is an underlying cause of certain types of congestive heart failure.

Treatment with TB4 significantly reduced left ventricular end diastolic pressure (LVEDP). Hypertension and/or elevated ventricular end diastolic pressures are/is a cause of certain type of congestive heart failure.

Ventricular Volume Reduction

Treatment with TB4 significantly attenuated left ventricular end systolic volume, which is elevated in patients with CHF. Because end systolic volume is a measurement of the adequacy of cardiac emptying related to systolic function, it is associated with CHF patients with systolic heart failure.

Treatment with TB4 significantly attenuated left ventricular end diastolic volume. In the diseased heart, cardiac output falls if ventricular end diastolic volume rises to high levels as is the case in heart failure. Left ventricular end diastolic volume increases are associated with CHF patients with diastolic heart failure.

Treatment with TB4 significantly improved rate of change (velocity) in left ventricular pressure-rise with time (dP/dt), a surrogate measure of ventricular contractility. Because there is only a finite period of time available for an ejection, a reduced ventricular pressure-rise rate of velocity (i.e., a longer time to contraction) results in less blood ejected per stroke. This is evidenced in CHF patients with systolic heart failure.

Treatment with TB4 showed a trend in affecting (improving) the rate of change (velocity) in left ventricular relaxation. The more negative the dP/dt the faster the heart is able to relax. CHF patients with diastolic heart failure have hearts that are less compliant, when relaxing and filing with blood. This impedes blood filling into the ventricles and produces backup into the lungs.

Organ Weights

Treatment with TB4 significantly attenuated pulmonary edema following heart muscle damage/injury. Pulmonary edema is a serious outcome that occurs in patients with CHF as a result of left-sided heart failure.

Treatment of TB4 significantly attenuated thickening muscle of the left ventricle that negatively affect the pumping action of the heart.

In this study, organ weights (heart and lung) in the TB4-treated, vehicle-treated and untreated animal (sham) groups were assessed. These data showed that TB4 attenuated both thickening of the heart muscle due to stress/injury and pulmonary edema (fluid build up in the lung due to left-sided heart failure), strongly indicating that TB4 may be effective in treating patients with congestive heart failure (CHF). Since CHF (also called heart failure) is almost always a chronic, long-term condition, chronic treatment by TB4 may retard or halt the progression of a worsening condition.

EXAMPLE 2

The use of thymosin beta 4 was studied during the development of dystrophic cardiomyopathy. We used the naturally occurring dystrophin deficient mdx mouse model and followed the cardiac function longitudinally with non-invasive echocardiography. Thymosin beta 4 may have beneficial effects on slowing the progression of the cardiomyopathy through its properties of membrane stabilization and anti-fibrosis. In dystrophic cardiomyopathies, shear forces are poorly tolerated due to the lack of the dystrophin and its connections to the extracellular matrix. These forces lead to tearing of the muscle cell membranes leading to cell death and fibrosis. Thymosin beta 4 has been shown to have membrane stabilizing properties, likely related to effects on actin polymerization. We also followed functional parameters of skeletal muscle function that may also benefit from administration of thymosin beta 4. Preliminary data is presented in table 1. Thymosin beta 4 also has anti-fibrotic properties. Cardiac muscle injured due to shear forces and calcium influx may benefit from thymosin beta 4's modulation of muscular remodeling. Less fibrosis maintains cardiac function for a longer period of time.

Test Parameters and Experimental Design:

Four groups of mice were treated with thymosin beta 4. Group 1 was normal mice (BL10) that were given placebo (untreated). Group 2 was normal mice that were treated with thymosin beta 4. Group 3 was dystrophin deficient (mdx) mice treated with placebo and Group 4 was mdx mice treated with thymosin beta 4. Mice were treated with 150 micrograms of thymosin beta 4 in 300 microliters of buffer given intraperitoneally twice a week and placebo mice were given 300 microliters of buffer only. The mice exercised on a treadmill at a speed of 12 meters/minute for 30 minutes twice a week. Functional, behavioral and echocardiographic data were obtained at baseline and after 2 months, 4 months and 6 months of treatment.

Functional data were non-invasive measurements of skeletal muscle function. The muscle strength of the forelimbs and hindlimbs was assessed using a grip strength meter. The animals were allowed to hold onto the meter platform and then were slowly pulled until they lost their grip. The amount of force needed to free the grip was recorded. Multiple measurements were taken for each mouse at each time point. The same protocol was followed for hindlimb muscle strength. Another functional assessment was the Rotarod test. Here, mice were placed on a rotating bar and kept their balance and position as the bar rotated with increasing speed (10 RPM for 1 minute and then increased 0.2 RPM over the next three minutes). The time until the mouse falls was measured. This test was also repeated multiple times.

Behavioral data was collected using the VERSAMAX™ animal activity monitoring system. Mice were placed in a monitored box and activity was quantified by different sensors. Data includes horizontal activity, vertical activity and total distance traveled and many other activity parameters were measured. Multiple measurements were made over a 3 day period.

Echocardiographic assessment was performed using the VISUALSONICS VEVO 660™ high frequency system. Evaluation of cardiac chamber size, ventricular function and inflow/outflow Doppler velocities were completed under isoflorane anesthesia. The cardiologist performing and measuring the echocardiograms was blinded to study groups.

TABLE 1

Functional parameters measured in normal (BL10) and dystrophin deficient (mdx) mice at baseline and after two months of treatment with thymosin beta 4.

| Time | Group | | | | | | | |
|---|---|---|---|---|---|---|---|---|
| | BL10 untreated Baseline | BL10 untreated 2 month | BL10 treated Baseline | BL10 treated 2 month | Mdx untreated Baseline | Mdx untreated 2 month | Mdx treated Baseline | Mdx treated 2 month |
| Avg max forelimb strength (KGF/kg) | 5.57 | 6.10 | 5.57 | 5.73 | 4.46 | 4.07 | 4.46 | 3.78 |
| Avg max hindlimb strength (KGF/kg) | 7.35 | 9.01 | 7.35 | 9.18 | 6.29 | 7.54 | 6.29 | 7.29 |
| Avg horizontal activity | 1761 | 1302 | 1761 | 1287 | 1071 | 875 | 1071 | 961 |
| Avg vertical activity | 28 | 15.6 | 28 | 13.1 | 12 | 9.0 | 12 | 8.2 |

TABLE 1-continued

Functional parameters measured in normal (BL10) and dystrophin deficient (mdx) mice at baseline and after two months of treatment with thymosin beta 4.

| Time | Group | | | | | | | |
|---|---|---|---|---|---|---|---|---|
| | BL10 untreated Baseline | BL10 untreated 2 month | BL10 treated Baseline | BL10 treated 2 month | Mdx untreated Baseline | Mdx untreated 2 month | Mdx treated Baseline | Mdx treated 2 month |
| Avg total distance (cm) | 375 | 252 | 375 | 239 | 209 | 162 | 209 | 167 |
| Avg movement time (s) | 41 | 28.4 | 41 | 27 | 25 | 19.2 | 25 | 18.9 |
| Rotorod | 214 | 170 | 214 | 191 | 211 | 172 | 211 | 147 |

The invention claimed is:

1. A method of treatment for treating, preventing, inhibiting or reducing tissue deterioration, injury or damage due to congestive heart failure disease, or for restoring tissue adversely affected by said disease, in a subject, comprising administering to a subject having congestive heart failure disease an effective amount of a composition comprising a peptide agent comprising amino acid sequence LKKTET (SEQ ID NO: 1) or a conservative variant thereof, LKKTNT (SEQ ID NO: 2) or a conservative variant thereof, Thymosin β4 (Tβ4), a Tβ4isoform, KLKKTET (SEQ ID NO: 3), LKKTETQ (SEQ ID NO: 4), oxidized Tβ4, an N-terminal variant of Tβ4, a C-terminal variant of Tβ4, Tβ4$^{ala}$, Tβ9, Tβ10, Tβ11, Tβ12, Tβ13, Tβ14, Tβ15, gelsolin, vitamin D binding protein (DBP), profilin, cofilin, depactin, DNaseI, vilin, fragmin, severin, capping protein, β-actinin or acumentin, in said tissue, so as to inhibit said tissue deterioration, injury or damage due to said disease, or restore tissue adversely affected by said disease, wherein administration of said peptide agent results in at least one of a reduction of left ventricular systolic pressure (LVSP) of a heart, reduction in left ventricular end diastolic pressure (LVEDP) of a heart, attenuation of left ventricular end systolic volume of a heart, attenuation of left ventricular end diastolic volume of a heart, an increase in rate of change (velocity) in left ventricular pressure-rise with time (dP/dt) of a heart, an increase in rate of change (velocity) in left ventricular pressure decrease with time (pdP/dt) of a heart, attenuation of pulmonary edema following heart muscle damage/injury, or attenuation of muscle thickness of a heart left ventricle.

2. The method of claim 1, wherein said tissue deterioration, injury or damage comprises at least one of an increase in heart size or mass, increase in size or mass of heart tissue, thickening of heart muscle, or pulmonary edema.

3. The method of claim 2 wherein said peptide agent is Tβ4.

4. The method of claim 2 wherein said peptide agent is other than Tβ4.

5. The method of claim 2 wherein said peptide agent is other than oxidized Tβ4.

6. The method of claim 4 wherein said peptide agent comprises amino acid sequence KLKKTET (SEQ ID NO: 3), amino acid sequence LKKTETQ (SEQ ID NO:4), and N-terminal variant of Tβ4, a C-terminal variant of Tβ4, or an isoform of Tβ4.

7. The method of claim 2 wherein said peptide agent is administered to said subject at a dosage within a range of about 1-30 micrograms.

8. The method of claim 2 wherein said agent is administered by direct administration to said tissue, or by intravenous, intraperitoneal, intramuscular, subcutaneous, inhalation, transdermal or oral administration, to said subject.

9. The method of claim 2 wherein said composition is administered systemically.

10. The method of claim 2 wherein said composition is administered directly.

11. The method of claim 2 wherein said composition is in a form of a solution, gel, cream, paste, lotion, spray, suspension, dispersion, salve, hydrogel, ointment, foam or oil.

12. The method of claim 2 wherein said peptide agent is a recombinant or synthetic peptide.

13. A method for screening for a stimulating agent that stimulates production of a peptide agent comprising amino acid sequence LKKTET (SEQ ID NO: 1) or a conservative variant thereof, LKKTNT (SEQ ID NO: 2) or a conservative variant thereof, Thymosin β4 (Tβ4), a Tβ4isoform, KLKKTET (SEQ ID NO: 3), LKKTETQ (SEQ ID NO: 4), oxidized Tβ4, an N-terminal variant of Tβ4a C-terminal variant of Tβ4, Tβ4$^{ala,}$ Tβ9, Tβ10, Tβ11, Tβ12, Tβ13, Tβ14, Tβ15, gelsolin, vitamin D binding protein (DBP), profilin, cofilin, depactin, DNaseI, vilin, fragmin, severin, capping protein, β-actinin or acumentin, comprising contacting a tissue exhibiting congestive heart failure disease, with a candidate compound; and measuring activity in said tissue of said peptide agent, wherein an increase of activity of said peptide agent in said tissue, compared to a level of activity of said peptide agent in a corresponding tissue lacking said candidate compound, indicates that said compound is capable of stimulating production of said peptide agent.

14. The method of claim 13 wherein said peptide agent is thymosin beta 4.

15. The method of claim 1, wherein said peptide agent is administered acutely, chronically, or a combination thereof.

* * * * *

SEQUENCE LISTING

```
<160> NUMBER OF SEQ ID NOS: 4

<210> SEQ ID NO 1
<211> LENGTH: 6
<212> TYPE: PRT
<213> ORGANISM: Homo sapiens

<400> SEQUENCE: 1

Leu Lys Lys Thr Glu Thr
1               5

<210> SEQ ID NO 2
<211> LENGTH: 6
<212> TYPE: PRT
<213> ORGANISM: Homo sapiens

<400> SEQUENCE: 2

Leu Lys Lys Thr Asn Thr
1               5

<210> SEQ ID NO 3
<211> LENGTH: 7
<212> TYPE: PRT
<213> ORGANISM: Homo sapiens

<400> SEQUENCE: 3

Lys Leu Lys Lys Thr Glu Thr
1               5

<210> SEQ ID NO 4
<211> LENGTH: 7
<212> TYPE: PRT
<213> ORGANISM: Homo sapiens

<400> SEQUENCE: 4

Leu Lys Lys Thr Glu Thr Gln
1               5
```